United States Patent [19]
Freer

[11] Patent Number: 6,097,981
[45] Date of Patent: Aug. 1, 2000

[54] ELECTROENCEPHALOGRAPH BASED BIOFEEDBACK SYSTEM AND METHOD

[75] Inventor: Peter A. Freer, Asheville, N.C.

[73] Assignee: Unique Logic and Technology, Inc., Asheville, N.C.

[21] Appl. No.: 08/982,774

[22] Filed: Dec. 2, 1997

Related U.S. Application Data

[63] Continuation-in-part of application No. 08/846,621, Apr. 30, 1997, abandoned.

[51] Int. Cl.[7] .................................................. A61B 5/04
[52] U.S. Cl. ................................. 600/545; 600/544
[58] Field of Search ...................... 600/544, 545

[56] References Cited

U.S. PATENT DOCUMENTS

| | | | |
|---|---|---|---|
| 4,140,997 | 2/1979 | Brady | 600/545 |
| 4,461,301 | 7/1984 | Ochs . | |
| 4,926,969 | 5/1990 | Wright et al. | 600/544 |
| 4,928,704 | 5/1990 | Hardt | 600/545 |
| 4,955,388 | 9/1990 | Silberstein | 600/544 |
| 5,213,338 | 5/1993 | Brotz | 600/544 |
| 5,219,322 | 6/1993 | Weathers | 600/27 |
| 5,279,305 | 1/1994 | Zimmerman et al. . | |
| 5,343,871 | 9/1994 | Bittman et al. | 600/545 |
| 5,377,100 | 12/1994 | Pope et al. | 600/545 |
| 5,447,166 | 9/1995 | Gevins | 600/544 |
| 5,540,235 | 7/1996 | Wilson | 600/545 |
| 5,571,057 | 11/1996 | Ayers . | |
| 5,740,812 | 4/1998 | Cowan . | |
| 5,755,230 | 5/1998 | Schmidt et al. | 600/545 |
| 5,899,867 | 5/1999 | Collura . | |

Primary Examiner—Cary O'Connor
Assistant Examiner—Navin Natnithithadha

[57] ABSTRACT

An apparatus and method with an electroencephalograph (EEG) based biofeedback system wherein a smooth, high quality computer animation is maintained while EEG responses are simultaneously being analyzed whereby the results of the analysis are then used to control the animation. EEG signals alone may be used to control computer animation. EEG signals may be sent from the head of the user to a remote receiver by infrared wireless transmission.

15 Claims, 11 Drawing Sheets

ELECTROENCEPHALOGRAPH BASED BIOFEEDBACK SYSTEM AND METHOD

CROSS-REFERENCE TO RELATED APPLICATION

This is a continuation-in-part of application Ser. No. 08/846,621, filed Apr. 30, 1997, and now abandoned.

FIELD OF INVENTION

The present invention relates generally to biofeedback systems and, more particularly, to an apparatus and method for improving the concentration of a user, and even more particularly, to an electroencephalograph (EEG) based biofeedback system and method. The present invention further relates to a novel EEG apparatus and method which utilizes infrared transmission.

BACKGROUND OF THE INVENTION

The ability to concentrate or pay enough attention to information allows the brain to transfer the information to short-term memory and then encode some of that information into long-term memory. Paying enough attention is the key.

According to the Minimal Stimulus Theory (MST), the attention of an individual is dependent upon certain thresholds of stimuli entering the brain to cause arousal or initiation of the process of attention. Some individuals require more stimulation than others. As used herein, the term "stimulation" is meant to include the elements of attention arousal including interest, motivation, and significance. If there is not enough stimulation, then attention is not aroused.

The capacity for sustained attention usually improves throughout childhood and early adolescence. The improvement in attention is due largely to the maturational changes in the central nervous system. The area of the brain responsible for the regulation of attention, i.e. the reticular formation, is not fully developed or myelinated until puberty. Myelination is the process by which neurons are encased in waxy myelin sheaths that facilitate transmission of neural impulses.

Trauma, lack of stimuli, disease, chemical imbalances, and various other factors affect the capacity of the brain to fully attend to tasks.

The present invention offers the user the opportunity to practice attention growth while simultaneously attending to those factors which comprise perception and which thus affect attention. Furthermore, the present invention may be implemented according to one or more educational cognitive psychology theories, especially those which focus on the development of attention or concentration.

Information processing begins with the perception of information, i.e. a stimulus. The information is accepted and held for a very brief period in a sensory memory store. Although the capacity of sensory memory appears to be unlimited, the mode of representation is sensory and thus the duration is very brief For example, visual information may last approximately one half second in sensory memory. Loss then occurs according to a time rate of decay.

The area of primary importance in the learning of new information begins when an individual selectively pays attention to the incoming stimulus before perception of the stimulus decays. Attention is selective. At any given moment, attention is focused on only a minute portion of the stimulation impinging on sensory receptors. During periods of focus, a person tries to concentrate attention on an object or event while ignoring irrelevant or distracting sensations. If a person is able to pay enough attention to the stimulus before it decays, some of the information may be transferred to short-term memory (STM). STM can be considered to be active consciousness or awareness. The capacity of STM appears to be quite limited. For example, a person may be able to think about only five things at one time. Thus, information input may be viewed as a modification of the sensory input and is therefore short in duration. Typically, items are lost after eighteen seconds unless there is active rehearsal. Moreover, loss may occur due to the introduction of new items in STM. A portion of the STM may be referred to as working memory which can be used to perform mental calculations.

Information may be encoded to long-term memory (LTM) if continued attention is paid to the information in the STM by means of rehearsal. Some of that information may be retained permanently. The LTM apparently has unlimited capacity and can retain information for long periods of time. Information may not effectively be encoded into the LTM when other competing information, or attention thereto, interferes with or taxes the rehearsal process. Information may also be lost from the LTM when other information interferes with retrieving the target information.

Other devices have been proposed which utilize EEG signals to provide some indication of the level of attention in a user.

Pope et al. disclose a method of enhancing the attention span of people. The method utilizes a host computer, a video game program including a joystick, and brain signal detecting and transmitting hardware. The method is accomplished by correlating the difficulty level of the video game program with the attention level of a user through the brain signal detecting and transmitting hardware.

Gevins discloses a neurocognitive adaptive computer interface system which monitors the EEG signals and physical responses of a user and uses these signals and responses to alter a computer program.

Brotz discloses a brain wave directed amusement device which permits two users to compete in a game using their own EEG signals. The EEG signals are detected and transmitted to a game controller via electrodes and brain wave monitors.

Silberstein discloses an EEG attention monitor comprising a display screen, electrodes connected to the scalp of a user, a computer, and a stimulus generator. The monitor detects the EEG signals from the user and uses these signals to determine the interest of the user in the displayed information.

Wright et al. disclose a sensory-driven controller comprising a display screen, a computer, EEG signal detecting electrodes, and computer to electrode interface hardware. The controller enables a user to perform various functions utilizing EEG signals. The system controller monitors EEG signals and transmits them to the computer.

Although all of the above-described patents are directed toward the monitoring of EEG signals for use in monitoring, utilizing, or affecting attention of a user, none are directed toward an apparatus and method for increasing attention (and enhancing relaxation) with an electroencephalograph (EEG) based biofeedback system wherein a smooth, high quality computer animation is maintained while EEG responses are simultaneously being analyzed whereby the results of the analysis are then used to control the animation.

The present invention preferably uses an educational protocol which incorporates hierarchical mastery of skills, including visual discrimination, auditory discrimination, and/or increased sensory perception.

Accordingly, it would be desirable to overcome the disadvantages of these prior art methods so as to provide an apparatus and method for improving concentration or attention, and further preferably promoting relaxation, with an EEG based biofeedback system wherein a smooth, high quality computer animation is maintained while EEG responses are simultaneously being analyzed whereby the results of the analysis are then used to control the animation.

SUMMARY OF THE INVENTION

The present invention contemplates an apparatus and method for improving attention with an electroencephalograph (EEG) based biofeedback system wherein a smooth, high quality computer animation is maintained while EEG responses are simultaneously being analyzed whereby the results of the analysis are then used to control the animation. EEG signals alone may be used to control a computer animation.

One embodiment of the present invention EEG based biofeedback system is particularly well suited to overcome the obstacle of the human eye being extremely sensitive to even slight interruptions of smooth motion. For example, slight pauses that could go unnoticed in a computer-based application program such as a word processor or a spreadsheet would appear as obvious glitches in smooth animation. This obstacle is overcome by the embodiment of the present invention EEG based biofeedback system through the use of two basic concepts.

First, the analysis of the EEG brain waves is not accomplished by the computer that is doing the animation. Rather, the analysis is performed by hardware frequency filters in a separate hardware unit. A set of three bandpass filters accepts the raw EEG input and outputs the amount of power in each of the three relevant frequency bands (i.e. alpha, beta, and theta frequency bands).

Second, the results of the frequency analysis are transmitted to a host computer in a way that does not disrupt the animation being performed by the host computer. This is accomplished by tuning the rate of data delivery from the separate hardware unit to the requirements of the host computer, and also by having the host computer trigger the delivery of new data. Thus, the reception of data by the host computer can be synchronized with the video frame changes, and thus blended smoothly with the animation.

Thus, in one aspect, the present invention concerns an apparatus for improving the attention of at least one user, the apparatus comprising means for generating and displaying a video animation, means for measuring electrical activity of the brain of the user, and means for altering the generation of the video animation in response to at least one user input, wherein the user input comprises the measured electrical activity. The means for altering the generation of the video animation preferably includes means for processing the measured electrical activity so as to be employable by the means for generating and displaying the video animation. The means for measuring electrical activity preferably includes at least one electroencephalographic (EEG) instrument.

The means for generating and displaying a video animation preferably includes at least one video display terminal. Preferably, the means for generating and displaying the video animation further includes means for maintaining the video animation while the measured electrical activity is simultaneously being processed.

In another aspect, the present invention concerns a game having means for generating a video animation, means for displaying the video animation, means for detecting at least one measurement of electrical activity of the brain of the user, and means for processing the electrical activity measurement into at least one indicator signal. The video animation generation means alters the video animation in response to the indicator signal. The game may be adapted to accommodate one or more users, either simultaneously or sequentially. For example, the electrical activity of the brain of at least two users may be detected and processed into at least two indicator signals.

In still another aspect, the present invention provides a biofeedback device for improving the concentration of at least one user. The biofeedback device includes means for generating a video animation, means for presenting the video animation, means for detecting at least one measurement which is indicative of the level of concentration of the user, and means for processing the measurement into at least one indicator signal. The video animation generation means alters the course of the video animation in response to the indicator signal, whereby the presentation of the video animation serves as feedback to the user corresponding to the level of concentration of the user.

Preferably, the detecting means detects an EEG response of the user, which is indicative of the level of concentration of the user. Further preferably, the detecting means detects at least one of beta waves and theta waves. In a particular embodiment, the detecting means detects both beta and theta waves. Thus, the processing means may convert at least one beta wave measurement and at least one theta wave measurement into at least one indicator signal, and the detecting means measures electrical activity of the brain of the user. the processing means preferably includes means for selectively filtering at least one frequency range of the electrical activity.

In one embodiment, the electrical activity measurement is the sole external factor upon which changes in the video animation are based.

The video animation may be altered in response to changes in the indicator signal, or the video animation may be altered in response to absolute levels of the indicator signal. The processing means is preferably capable of storing the measurement and comparing the measurement with at least one previously stored measurement. The processing means is further preferably capable of comparing the measurement to a threshold value.

In yet another aspect, the present invention concerns an apparatus which is capable of detecting at least one EEG signal of at least one user. The apparatus includes at least one EEG probe for picking up at least one electrical signal associated with the brain activity of a user, transmission means for converting the electrical signal into at least one infrared signal, and mounting means for maintaining the probe in contact with the head of the user and for mounting the transmission means on the head of the user. The apparatus preferably further includes an electrical power source, mounted on the mounting means, for energizing the transmission means.

The present invention may further comprise a system which includes such an apparatus, wherein the system further includes an infrared receiving means for receiving the infrared signal from the apparatus and generating at least one EEG signal. In a highly preferred embodiment, the apparatus and the receiving means are untethered.

The system further preferably includes a computer means and means for delivering the EEG signal to the computer means. The computer means would typically include a computer memory encoded with executable instructions representing a computer program. Preferably, the computer program is capable of causing the computer means to present a video game. Furthermore, the computer program is preferably capable of processing the EEG signal as an input into the video game.

In one embodiment, the computer program is capable of storing the EEG signal and comparing the EEG signal with at least one previously stored EEG signal. The computer program is further preferably capable of comparing the EEG signal to a threshold value. The computer program may also be capable of establishing a threshold value based upon at least one previous EEG signal. The threshold value may be stored in the computer memory. Thus, the computer program may be capable of adaptively or automatically changing the threshold value based upon a comparison between the EEG signal and at least one previous EEG signal.

In still another aspect, the present invention provides a method for improving the attention of at least one user. The method comprises the steps of: measuring electrical activity in the brain of a user; presenting a video game to the user; and controlling the video game with at least one user input, wherein the user input comprises the analyzed measured electrical activity. The method may further comprise the step of analyzing the measured electrical activity, wherein the user input further comprises the analyzed electrical activity. The electrical activity may correspond to alpha, beta, or theta waves. For example, beta and theta wave components are preferably measured in order to gauge the level of attention of a user.

In yet another aspect, the present invention comprises a method for improving the attention of at least one user by biofeedback. The method comprising the steps of: measuring electrical activity of the brain of a user; analyzing the measured electrical activity; presenting a video game having at least one game output to the user; inputting the analyzed electrical activity into the video game; and presenting to the user at least one feedback signal corresponding to the analyzed electrical activity, wherein the feedback signal is manifested by changes in the game output of the video game, whereby the user is rewarded by sensing the changes in the game output of the video game, and whereby the game output assists the user in controlling the electrical activity. The method also include providing active user inputs to the video game, such as those provided by actuation of a keyboard, mouse, trackball, pedal, touch screen, stylus, button, lever, touch pad, or the like. Preferably, the electrical activity is analyzed in a computer means having a processing means and a memory means. Furthermore, the method may include transmitting the electrical activity to the computer means by infrared signal.

Game output may include a variety of outputs to the user, such as video, audio, tactile, or other sensory reward.

A user may, for example, be rewarded for achieving at least one level of electrical activity, or for maintaining at least one level of electrical activity for a predetermined period of time.

The video game may further presents a plurality of visual images to the user, wherein the user is rewarded for identifying at least one association between at least two of the visual images and for inputting a direct user input corresponding to the association.

Alternately, or in addition, the video game may present at least one primary game output and at least one distracting game output to the user, wherein the user is rewarded for identifying the primary game output and for inputting a direct user input corresponding to the identification.

Thus, the present invention may embody, or be used in conjunction with, a protocol, such as an educational protocol or a training protocol, which incorporates hierarchical mastery of skills, including visual discrimination, auditory discrimination, and/or increased sensory perception.

Accordingly, a primary object of the present invention is to provide an apparatus and method for promoting attention or concentration, and further preferably enhancing relaxation, of a user with an electroencephalograph (EEG) based biofeedback system wherein a smooth, high quality computer animation is maintained while EEG responses are simultaneously being analyzed whereby the results of the analysis are then used to control the animation.

The above primary object, as well as other objects, features, and advantages, of the present invention will become readily apparent from the following detailed description which is to be read in conjunction with the appended drawings.

BRIEF DESCRIPTION OF THE DRAWINGS

In order to facilitate a fuller understanding of the present invention, reference is now made to the appended drawings. These drawings should not be construed as limiting the present invention, but are intended to be exemplary only.

FIG. 9 illustrates a top view of a preferred headpiece according to the present invention comprising a particular electrode arrangement.

FIG. 10 illustrates a side elevational view of the headpiece of FIG. 9.

FIG. 11 illustrates a perspective view of the preferred headpiece according to the present invention as worn by a user.

DETAILED DESCRIPTION OF A PREFERRED EMBODIMENT

Figure 1:
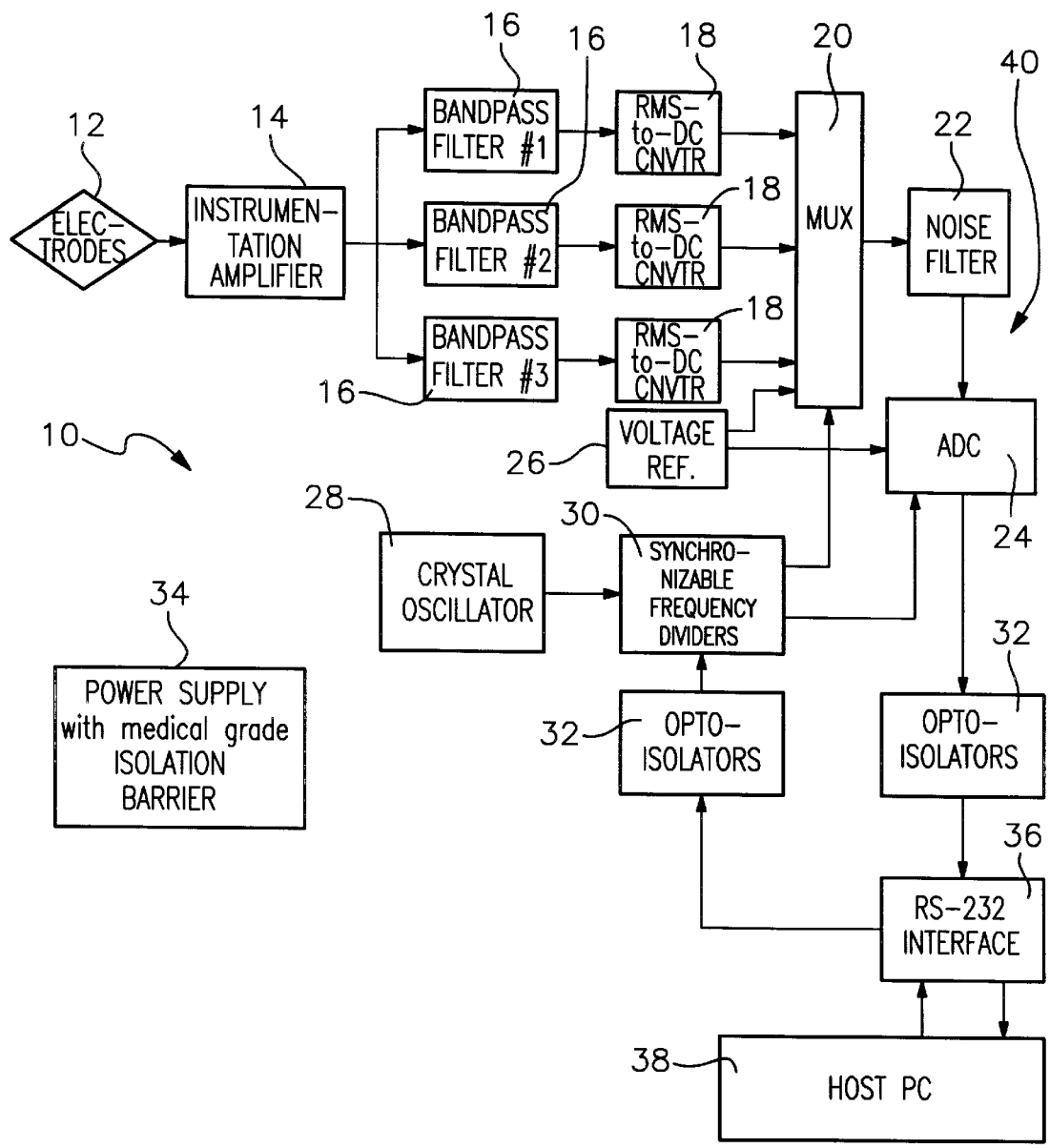
FIG. 1 is a schematic block diagram of one embodiment of an EEG based biofeedback system according to the present invention.

The present invention permits immediate and direct feedback on the attentive state wherein a user can actually hear and/or see when optimum attention is being paid to stimuli, and wherein the user is rewarded immediately, or nearly immediately, thereby encouraging the development of longer periods of sustained attention.

In one aspect, the present invention concerns an apparatus for improving the attention of at least one user, the apparatus comprising means for generating and displaying a video animation, means for measuring electrical activity of the brain of the user, and means for altering the generation of the video animation in response to at least one user input, wherein the user input comprises the measured electrical activity.

The means for altering the generation of the video animation preferably includes means for processing the measured electrical activity so as to be employable by the means for generating and displaying the video animation. The means for measuring electrical activity preferably includes at least one electroencephalographic (EEG) instrument. The means for generating and displaying a video animation preferably includes at least one video display terminal.

Preferably, the means for generating and displaying the video animation further includes means for maintaining the video animation while the measured electrical activity is simultaneously being processed.

In another aspect, the present invention concerns a game having means for generating a video animation, means for displaying the video animation, means for detecting at least one measurement of electrical activity of the brain of the user, and means for processing the electrical activity measurement into at least one indicator signal. The video animation generation means alters the video animation in response to the indicator signal.

In one embodiment, the measured electrical activity is the sole user input upon which changes in the video animation are based.

Preferably, the video animation is altered in response to changes in the indicator signal.

Furthermore, the processing means is capable of storing the electrical activity measurement and comparing the measurement with at least one previously stored measurement. The processing means may also be capable of comparing the electrical activity measurement to a threshold value.

The threshold value may be determined before the user plays the game, e.g. by a previously inserted or previously measured value. On the other hand, the present invention allows the threshold to be determined after electrical activity of the user has been detected. Thus, thresholds, which are particular to an individual or individuals who are currently interacting with the game, may be obtained from measurements corresponding to that user or other users. While the present invention permits setting thresholds obtained in this manner before a "play session" or "training session," i.e. during a calibration session, the present invention further permits setting thresholds "on the fly" i.e. during a play session or training session, without the need to set thresholds in a calibration session.

Thus, according to the present invention, the user can interact immediately with the game without first being subjected to a battery of tasks or tests in order to establish a baseline or a response template which would then serve as a threshold basis. Furthermore, according to the present invention, thresholds may be determined during the course of a play or training session, e.g. a running threshold may established which adaptively or automatically adjusts to the progress of the user. Thus, the processing means is capable of adaptively or automatically changing the threshold value based upon a comparison between the measurement and at least one previous measurement. Preferably, the processing means is capable of establishing a threshold value based upon at least one previous measurement, for comparison with the electrical activity currently being measured. Thus, the threshold value may be established while the user plays the game.

The present invention may be adapted to accommodate one or more users, either simultaneously or sequentially. For example, the electrical activity of the brain of at least two users may be detected and processed into at least two indicator signals.

In still another aspect, the present invention provides a biofeedback device for improving the concentration of at least one user. The biofeedback device includes means for generating a video animation, means for presenting the video animation, means for detecting at least one measurement which is indicative of the level of concentration of the user, and means for processing the measurement into at least one indicator signal. The video animation generation means alters the course of the video animation in response to the indicator signal, whereby the presentation of the video animation serves as feedback to the user corresponding to the level of concentration of the user.

Preferably, the detecting means detects an EEG response of the user, which is indicative of the level of concentration of the user. Further preferably, the detecting means detects at least one of beta waves and theta waves. In a particular embodiment, the detecting means detects both beta and theta waves. Thus, the processing means may convert at least one beta wave measurement and at least one theta wave measurement into at least one indicator signal, and the detecting means measures electrical activity of the brain of the user.

The processing means preferably includes means for selectively filtering at least one frequency range of the electrical activity.

In one embodiment, the electrical activity measurement is the sole external factor upon which changes in the video animation are based.

The video animation may be altered in response to changes in the indicator signal, or the video animation may be altered in response to absolute levels of the indicator signal.

The processing means is preferably capable of storing the measurement and comparing the measurement with at least one previously stored measurement. The processing means is further preferably capable of comparing the measurement to a threshold value.

In one embodiment, the threshold value is not predetermined before the user plays the game. In that embodiment, the threshold value, or values, is determined as the user plays the game, or the threshold value is set during a pre-game threshold setting session. Furthermore, the processing means may be capable of adaptively or automatically changing the threshold value based upon a comparison between the measurement and at least one previous measurement. Thus, the processing means may be capable of establishing a threshold value based upon at least one previous measurement. For example, the threshold value may be established while the user plays the game.

In yet another aspect, the present invention concerns an apparatus which is capable of detecting at least one EEG signal of at least one user. The apparatus includes at least one EEG probe for picking up at least one electrical signal associated with the brain activity of a user, transmission means for converting the electrical signal into at least one infrared signal, and mounting means for maintaining the probe in contact with the head of the user and for mounting the transmission means on the head of the user.

The apparatus preferably further includes an electrical power source, mounted on the mounting means, for energizing the transmission means.

The present invention may further comprise a system which includes such an apparatus, wherein the system further includes an infrared receiving means for receiving the infrared signal from the apparatus and generating at least one EEG signal. In a highly preferred embodiment, the apparatus and the receiving means are untethered.

The system further preferably includes a computer means and means for delivering the EEG signal to the computer means. The computer means would typically include a computer memory encoded with executable instructions representing a computer program. Preferably, the computer program is capable of causing the computer means to present a video game. Furthermore, the computer program is preferably capable of processing the EEG signal as an input into the video game.

In one embodiment, the computer program is capable of storing the EEG signal and comparing the EEG signal with at least one previously stored EEG signal. The computer program is further preferably capable of comparing the EEG signal to a threshold value. The computer program may also be capable of establishing a threshold value based upon at least one previous EEG signal. The threshold value may be stored in the computer memory. Thus, the computer program may be capable of adaptively or automatically changing the threshold value based upon a comparison between the EEG signal and at least one previous EEG signal.

In still another aspect, the present invention provides a method for improving the attention of at least one user. The method comprises the steps of: measuring electrical activity in the brain of a user; presenting a video game to the user; and controlling the video game with at least one user input, wherein the user input comprises the analyzed measured electrical activity. The method may further comprise the step of analyzing the measured electrical activity, wherein the user input further comprises the analyzed electrical activity.

In one embodiment, the analyzed electrical activity is the sole user input for controlling the progress of the video game.

The electrical activity may correspond to alpha, beta, or theta waves. For example, beta and theta wave components are preferably measured in order to gauge the level of attention of a user.

Thus, the step of measuring electrical activity may include measuring electrical activity in the brain of a user using an electroencephalograph (EEG) instrument.

The step of controlling the video game preferably includes maintaining a video animation while the measured electrical activity is simultaneously being analyzed.

In yet another aspect, the present invention comprises a method for improving the attention of at least one user by biofeedback. The method comprising the steps of: measuring electrical activity of the brain of a user; analyzing the measured electrical activity; presenting a video game having at least one game output to the user; inputting the analyzed electrical activity into the video game; and presenting to the user at least one feedback signal corresponding to the analyzed electrical activity, wherein the feedback signal is manifested by changes in the game output of the video game, whereby the user is rewarded by sensing the changes in the game output of the video game, and whereby the game output assists the user in controlling the electrical activity.

The method also include providing active user inputs to the video game, such as those provided by actuation of a keyboard, mouse, trackball, pedal, touch screen, stylus, button, lever, touch pad, or the like.

Preferably, the electrical activity is analyzed in a computer means having a processing means and a memory means.

Furthermore, the method may include transmitting the electrical activity to the computer means by infrared signal.

Game output may include a variety of outputs to the user, such as video, audio, tactile, or other sensory reward.

A user may, for example, be rewarded for achieving at least one level of electrical activity, or for maintaining at least one level of electrical activity for a predetermined period of time.

The video game may further presents a plurality of visual images to the user, wherein the user is rewarded for identifying at least one association between at least two of the visual images and for inputting a direct user input corresponding to the association.

Alternately, or in addition, the video game may present at least one primary game output and at least one distracting game output to the user, wherein the user is rewarded for identifying the primary game output and for inputting a direct user input corresponding to the identification.

Thus, the present invention may embody, or be used in conjunction with, a protocol, such as an educational protocol or a training protocol, which incorporates hierarchical mastery of skills, including visual discrimination, auditory discrimination, and/or increased sensory perception.

In one embodiment, the present invention a method which incorporates a pedagogy, which preferably comprises a series of steps or phases of training which progressively build skills that increase the ability of the user to retain and attend to stimuli while disregarding and/or ignoring irrelevant or distracting information. Each phase preferably helps the user to build upon progress in improving concentration that was attained in previous phases.

In a particular embodiment, the present invention comprises a method comprising six phases.

Phase 1 teaches the user to learn how to pay optimum attention with the aid of a coach. Coaching provides the user with encouragement and reinforcement, especially when the user experiences an inability to pay attention. A user may be rewarded for appropriate levels of attention, for example through the use of visual cues, scoring and/or auditory tones. Thus, initial user training which is directed to increasing attention and thus increasing the capacity for processing information may be achieved by the present invention.

Phase 2 encourages the user to operate a device, particularly a device controlled by circuit logic or program logic or software and more particularly, a video game, and thus lengthen the attentive state, without the need of a coach. Changes in one or more measured states, preferably corresponding to a measure of the attentive state in the user, most preferably EEG signals, cause changes in the output or progress or outcome of at least part of a game in which the user plays. Thus, Phase 2 preferably builds upon Phase 1 by allowing the user to experience game changes when optimum attention is paid for extended periods. For example, the user may begin playing with one video game or one phase of the game, whereafter the user is allowed to proceed to the next game or next phase of the game when optimum attention is paid for a five to seven minute period without the use of coaching. Thus, the user is taught and rewarded to extend the attentive state. Furthermore, according to at least one theory of information processing, such encouragement of the attentive state is of importance in, and increases the capacity of, the ability to transfer information (stimulus) into the sensory memory.

Phase 3 further reinforces the attentive state, thereby strengthening the ability of the user to process information (stimulus) into the sensory memory. Preferably, the user begins by optimizing the attentive state as learned in Phases 1 and 2. For example, the user may effect changes in screen color by achieving a maximum attention level as compared to previously attained by a critical base line. Once the maximum attentive state is achieved, the user may view one or more visual forms which represent wholes and parts of identifiable figures. For example, geometric figures may appear on the left side of the screen, while the right side of the screen may depict a portion of the geometric figure which is shown on the left side of the screen. The user must discern, as quickly as possible, if the figures are somehow related. The user will also perform the same task with partial figures of known animals or objects, wherein the user discriminates the completed animal or object from a list on the right side of the screen which may contain an image of the whole animal or object or a portion thereof The tasks thus teach the user to quickly discern or discriminate the presence of objects and parts while maintaining optimum attention. Preferably, Phase 3 prepares the user or learner to proceed to Phase 4.

Phase 4 teaches the user to maintain optimum attention (for example, by feedback provided by screen color cues) while performing a discriminatory search, such as a visual search of images which exercises the processing of information into the STM. For example, geometric designs may be viewed on the left side of a split screen. The designs may be surrounded by distracting stimuli. One object in this phase is for the user to determine the category of the design or figure as quickly as possible. In another embodiment, a similar test may be presented by auditory tones. This phase of training teaches the user to pay maximum attention while disregarding unnecessary stimuli. Thus, in a progressive sequence of phases of training, the user will have learned to pay optimum attention without coaching, to discern that which is appropriate stimuli, and to disregard irrelevant stimuli.

Phase 5 preferably reinforces Phase 4, and further prepares the user for Phase 6, by teaching the user to pay optimum attention while being monitored by a continuous performance test. The test requires the user to play one or more video games at optimum attention levels. For example, during this session, target images are displayed in a manner as to appear in the path of a flying object. One object is for the user to quickly fire upon the object unless the object is a pre-directed non-target. The rapidity or pace of the games forces the user to selectively discriminate between appropriate data/stimuli and inappropriate data/stimuli. A control means or software preferably monitors the reaction speed, accuracy of hits and misses, and impulsivity of the user. This particular phase teaches the user to not only discriminate between distracting data and relevant data, but to be encouraged when the user is significantly engaging the areas of the STM and working memory which are necessary for information to become encoded in the LTM.

Phase 6 effectively combines the previous phases into a single application, so as to be beneficial for improving the encoding of information into the LTM. This phase also closely simulates educational and clerical processes by allowing the user to maintain optimum attention while transposing data from the left split screen to the right split screen, which may be accomplished, for example, by a manual user input such as through a keyboard, mouse, trackball, pedal, etc. For example, data may consist of words, phrases, mathematical equations, and/or geometric shapes. The present invention therefore provides a training environment which encourages the process of transference, i.e. the ability to apply what one learns to a wider variety of situations and circumstances.

In a preferred embodiment, the present invention comprises an EEG (electroencephalograph) collection unit connected to a personal computer by an interface unit.

In one particular embodiment, the average millivolt theta activity of a user is determined, whereafter theta thresholds for a user are preferably set at 1 to 2 millivolts lower than the user's average millivolt theta activity. Furthermore, beta thresholds may be set at average millivolt beta activity levels. Averages of theta and beta thresholds may be obtained during a 45 second base line without feedback. It has found that the user may thus immediately, or nearly immediately, perceive his or her level of attention during the biofeedback session in which the user receives some indication of the level or change in level of a variable which corresponds to a measure of the attention level of the user. By way of biofeedback, the present invention encourages the decrease of theta wave activity and the increase of beta wave activity, in a particularly preferred embodiment, by providing rewards 0.005 second after the subject achieves 1 to 2 millivolts decrease in theta and 1 to 2 millivolts in beta activity. It has been found through testing that such a reward scheme is optimal in maximizing the attention and/or concentration of the user, and concomitantly, the relaxation of the user.

Feedback presented to the user may take the form of auditory tones and/or visual graphics as typically presented in the form of video games. For example, further token reinforcement may be supplied by on-screen scoring. In one particular embodiment utilizing a video game, the subject can make a fish dive to the bottom of a video ocean as theta thresholds are decreased and beta increased, thus scoring higher points as displayed on the screen. Furthermore, any increase in theta activity will cause the fish to go in the opposite direction necessary to score points. When the subject achieves over 25 rewards per minute on a consistent basis, the threshold (either theta or beta) may be made more difficult.

A feedback scheme or algorithm according to the present invention may further include lowering one or more thresholds, thereby decreasing the demands on the user for achieving measurable success, when the user otherwise fails to achieve the desired brainwave activity, and thus, concentration levels.

Referring to FIG. 1, there is shown a schematic block diagram of a first embodiment of the present invention EEG based biofeedback system 10. The EEG based biofeedback system 10 comprises electrodes 12, an instrumentation amplifier 14, bandpass filters 16, RMS-to-DC converters 18, an analog multiplexer 20, noise filtering 22, an analog-to-digital converter (ADC) 24, a voltage reference 26, a crystal oscillator 28, synchronizable frequency dividers 30, opto-isolators 32, a power supply 34, an RS-232 serial data interface 36, and a host personal computer (PC) 38.

The electrodes 12, which are placed on the head of a user, are used to pick up the very low level (micro volts) EEG signals. These signals are then conveyed via cables to the instrumentation amplifier 14. The instrumentation amplifier 14 is a low level, low noise, floating, differential input, high common mode rejection amplifier. The instrumentation amplifier 14 performs the function of extracting the very weak EEG signals from its typical noisy environment.

The bandpass filters 16 are necessary to separate the various bands of brain wave activity. This separation function is performed by analog filters as shown in FIG. 1. The filtering must be precise and selective to perform this function.

The RMS-to-DC converters 18 are used to detect the magnitude of brain wave activity within each band of interest. The detected signals are used to reduce the bandwidth of data that must be digitized and sent to the host PC 38.

The analog multiplexer (MUX) 20 is an electronic switch used as a data selector to present to the ADC 24 only the data channel that has been selected for analog to digital conversion.

The noise filtering 22 is used to remove both random noise and spikes that are generated by other electronic switching circuits within the system.

The ADC 24 is used to convert the analog signal (selected by the MUX 20) into a digital (or numerical) value. As a matter of convenience, the ADC 24 used here provides a serial data output stream for each conversion made.

The voltage reference 26 is needed for the ADC to convert unknown signal levels into calibrated DC voltages. The voltage reference 26 is also injected as one of the MUX 20 input channels so that the software running on the host PC 38 can verify proper operation of the circuitry.

The crystal oscillator 28 provides a time base. This time base serves several necessary functions. First, it is the "clock" frequency used by the ADC 24 to perform its conversions. Second, the particular frequency chosen provides, through a simple integer division ratio, one of the standard RS-232 baud rates for the serial data communications through the RS-232 serial data interface 36. Third, the master crystal oscillator frequency is divided down by a variety of different integers to set the programmable filters which comprise the bandpass filter set 16. Lastly, a pair of resettable dividers provide a synchronizable low frequency that is used to trigger the ADC 24.

The synchronizable frequency dividers 30 are used not only to trigger the ADC 24 as mentioned above, but also to synchronize software commands to insure that the data to the host PC 38 maintains an integral relationship to the frame rate of an associated video monitor. This is essential in providing flicker free performance of the animation while simultaneously collecting and analyzing the digitized brain wave data (in real time) that is used to control the animation. This type of divider circuit provides a constant frequency output that is just slightly altered to bring it into synchronization with a synchronizing pulse, which in this case is sent by the host PC 38.

The opto-isolators 32 are used to provide a very high degree of electrical isolation between the user (with electrodes connected) and the computer system.

The power supply 34 is needed for the main electronic circuits. Preferably, a power supply having a high isolation barrier is maintained between the user and the AC power line which is connected to the power supply 34.

The RS-232 serial data interface 36 provides for the serial data communications between the host PC 38 and the other circuitry. Before the isolated serial data can be transferred to and from the host PC 38, the signal levels must be changed to the standard RS-232 signal levels (from the typical 5 volt logic levels). The RS-232 serial data interface 36 typically interfaces with the mouse port of the host PC 38.

The host PC 38 provides two distinct and essential functions for the present invention EEG based biofeedback system 10. First, it runs the animation and the user interface that provides the feedback to the user. Second, and equally as important, it performs the inter-related functions of data collection and analysis. Without this second function (which preferably occurs in the background), there would be no control of the animation related to the user's brain wave activity.

Typically, all of the above-described components except for the host PC 38 are preferably contained in a separate hardware unit, designated hereinafter by numeral 40.

With all of the components of the first embodiment of the present invention EEG based biofeedback system 10 now individually described, the overall function of the present invention EEG based biofeedback system 10 can be easily explained.

The separate hardware unit 40 sends a two byte number specifying a voltage approximately every 67 msecs over the RS-232 line to the host PC 38. The arrival of each byte triggers a very brief, custom interrupt routine in the host PC 38. The interrupt routine determines whether the byte is the first or the second byte in the pair by checking a parity bit, and puts the data in the proper buffer memory location. It has been determined that this rate of RS-232 interrupts does not interfere with the animation.

The host PC 38, meanwhile, follows a cycle of selecting the brain wave to be sampled, reading the data, and using the data to control the animation. This cycle is important to keep the animation smooth by never trying to do too much at once during the cycle. Each step in the cycle lasts one video frame, the time between one video blanking signal and the next. The duration between video blanks is $\frac{1}{60}$ sec, about 66.67 msec. The video blanking signal is on when the electron beam in a cathode ray tube (CRT) monitor moves from the bottom right corner of the screen to the top left in order to begin painting the next video frame's image.

The entire cycle may comprise N steps or timing increments. In the first step, the host PC 38 sends a message to the separate hardware unit 40 or box which indicates which brain wave band is selected for data transmissions. Four such channels may be available: a reference voltage, a theta band, an alpha band, and a beta band. In the Nth step, the host PC 38 reads the data buffer memory and retrieves the last data placed there by the interrupt routine. It has been determined empirically that different host processor speeds require waiting a different number N' of video frames after triggering a new channel in order to let the electronics in the separate hardware unit 40 settle on the new channel and produce highly stable data. Finally, in the second step of the following cycle, the data is fed to the animation routine to move characters on the screen.

Thus, the interface interactions between the host PC 38 and the separate hardware unit 40 are synchronized to the video animation steps, and dispersed over a standard cycle into the first, second, and Nth steps or time increments. As a result, excessive activity during any one video frame is prevented. If too much activity is attempted during a video frame, then the next video image is not painted and presented soon enough (i.e., the next video frame is not sufficiently displayed), and the eye sees an irregularity in the motion. Typically, much of the activity of the host PC 38 during each video frame is dedicated toward updating the ongoing animation.

Figure 2:
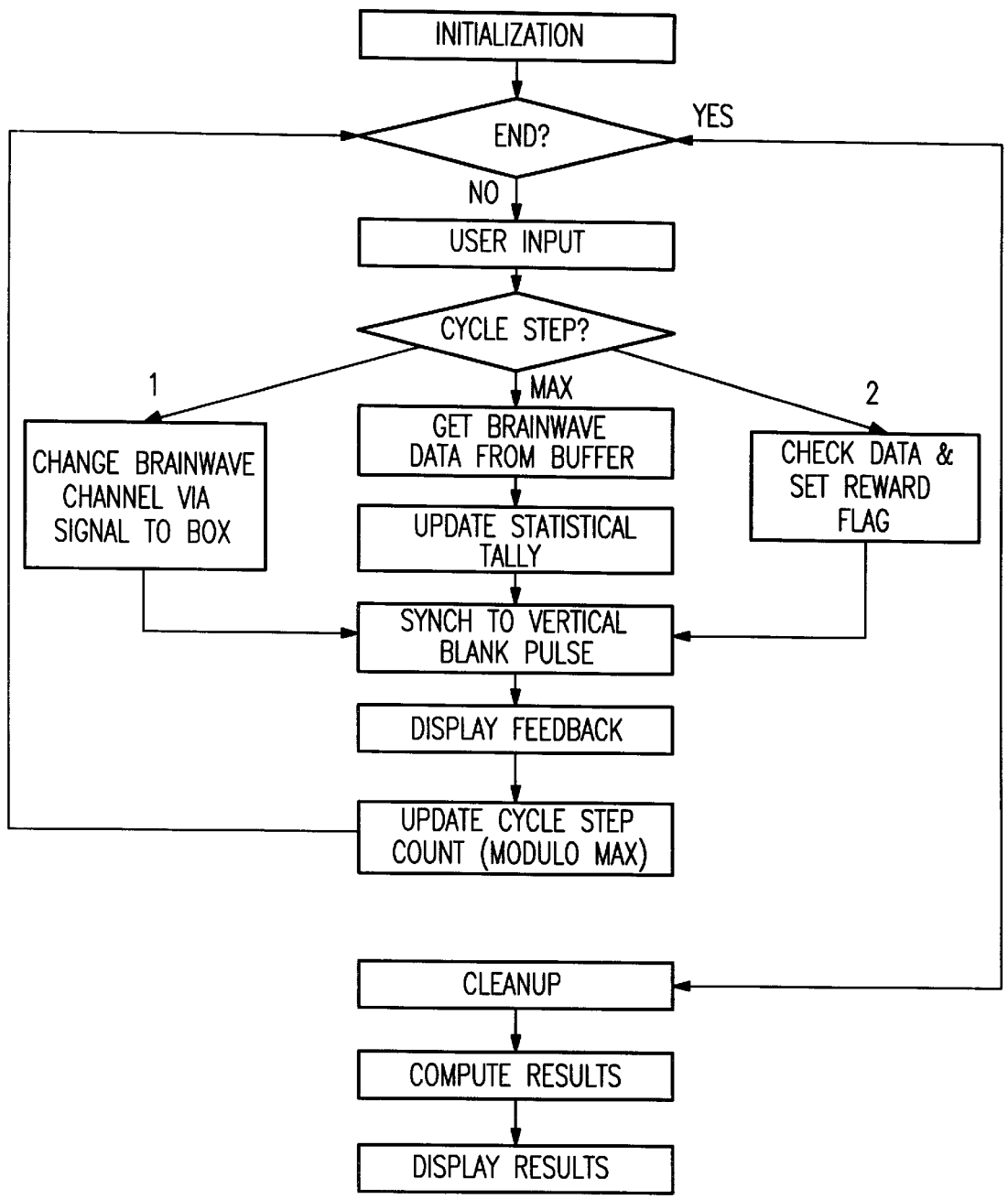
FIG. 2 is a flowchart diagram detailing the logic synchronizing the interface of a host computer to an external hardware unit in an EEG based biofeedback system according to the present invention.

FIG. 2 shows a flowchart diagram detailing the logic synchronizing the interface of the host PC 38 to the separate hardware unit 40. Three different tasks in interfacing with the separate hardware unit 40 are spread across several display cycles to avoid a jerky appearance in the animation. An interrupt handling routine places the brain wave data in the buffer for later retrieval. Data arrives from the box at some time between the first and the last (max) cycle step in the total cycle. The total cycle lasts "max" vertical blank cycles of the video display of the host PC 38.

One example of an animation that may be produced in connection with the present invention is that of an image of a bird flying across the video screen. When the user begins to lose attention, as determined from an analysis of one or more user EEG signals, the altitude of the bird begins to decrease. On the other hand, when the user is responding to the stimulus or stimuli (such as the video image) or when the user is fully attentive, the altitude of the bird either increases or is maintained at a constant level, respectively.

The attention level of the user may be measured by the present invention by detecting the energy levels corresponding to the alpha, beta, and theta frequency bands. The level of energy in these frequency bands, having approximate ranges of 8–12 Hz, 12–16 Hz, and 4–7 Hz, respectively, indicate the level of brain wave activity in the user, and thus may be used as a direct indication of the attention level of the user.

Figure 3:
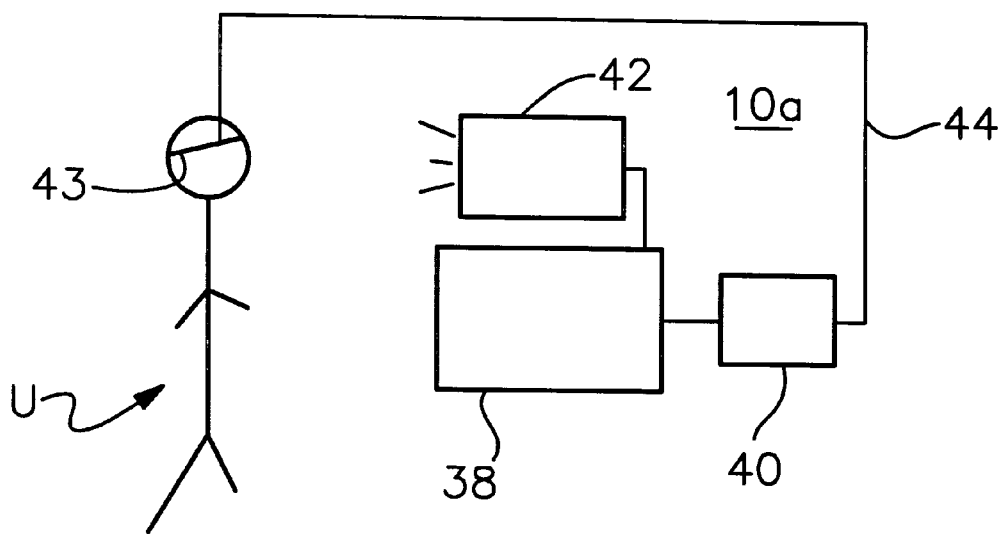
FIG. 3 is a schematic illustration of one embodiment of the present invention wherein a user uses an EEG based biofeedback system to gain proficiency in focusing and controlling attention by manipulating graphical characters on a video screen using the mind alone.

As schematically illustrated in FIG. 3, one embodiment of the present invention EEG based biofeedback system 10a allows a user U to rapidly gain proficiency in focusing and controlling attention by manipulating graphical characters on a video screen 42 using his or her mind alone. The user dons one or more electrodes, which may be optionally mounted on a headpiece 43, which are connected to hardware unit 40 by connection line 44, and the hardware unit 40 is connected to the host PC 38 which drives a peripheral such as a video screen 42 or audio speaker.

According to one theory, the present invention is capable of teaching mastery of attention by the stimulation or activation of a natural neural system which may have heretofore been dormant.

Figure 4:
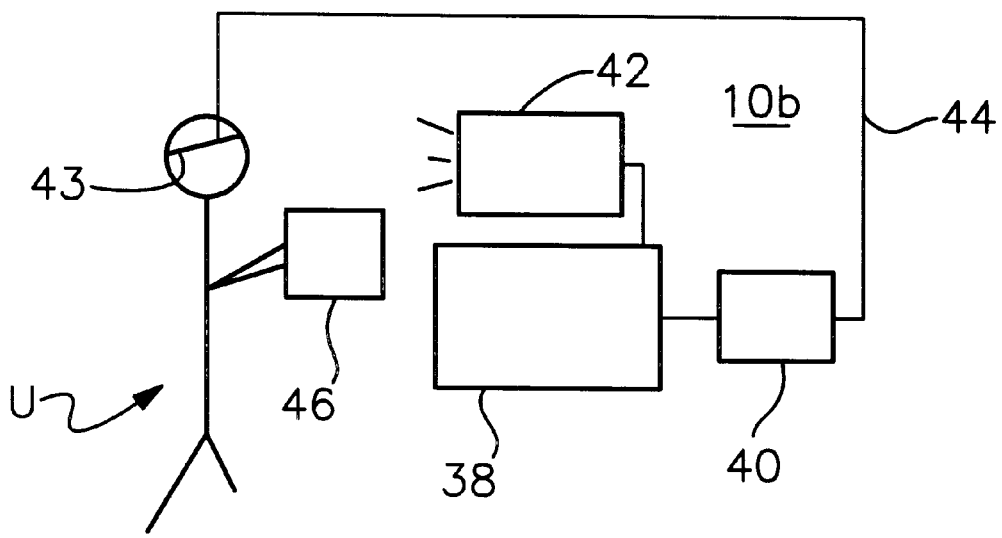
FIG. 4 is a schematic illustration of another embodiment of the present invention, similar to the embodiment shown in FIG. 3, further comprising other modes of input or physical control means.

Through the use of the present invention EEG based biofeedback system 10a a user U can learn to directly control and manipulate action on a computer video screen 42 solely or totally by using his or her attention. This self-learning process may trigger unutilized or underutilized neural pathways or may further trigger the formation of new neural networks and schema. Thus, the user may actually learn how to pay increasing attention to lower and lower levels of stimulation while developing an increased physio-mental capacity for such tasks. Thus, the present invention EEG based biofeedback system 10a may utilize only the mind of a user to control the computer animation. The computer keyboard or other physical control means are required only when turning the computer on or off In another embodiment, as schematically represented in FIG. 4, the present invention 10b may further utilize other modes of input or physical control means or active user input 46, such as a computer keyboard or joystick, in conjunction with EEG signals in providing the user U with feedback and/or in controlling and manipulating action on a video screen 42.

In yet another embodiment of the present invention, an EEG based biofeedback system comprises a probe head piece which does not rely on a physical connection line between the user and another piece of equipment. The headpiece is untethered with respect to other system components. In a particular embodiment, the system includes a probe head piece having one or more EEG electrodes, and an infrared transmission unit connected to the electrodes.

Figure 5:
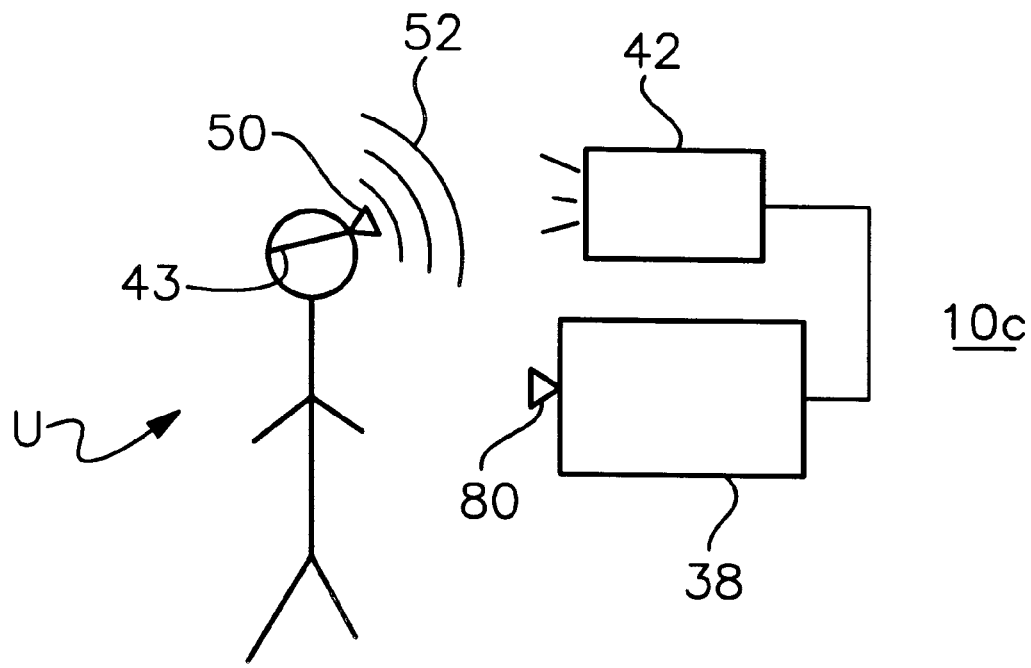
FIG. 5 schematically illustrates another embodiment of the present invention wherein a user wears a headpiece containing EEG probes and an infrared transmitter to gain proficiency in focusing and controlling attention by manipulating a video screen using the mind alone.

FIG. 5 schematically illustrates such an embodiment of the present invention 10c wherein the user U dons a headpiece 43 containing EEG probes and an infrared transmitter 50 having a battery source and a microprocessor. The headpiece 43 transmits signals corresponding to the EEG readings, via infrared radiation, as denoted by the lines and reference numeral 52.

Figure 6:
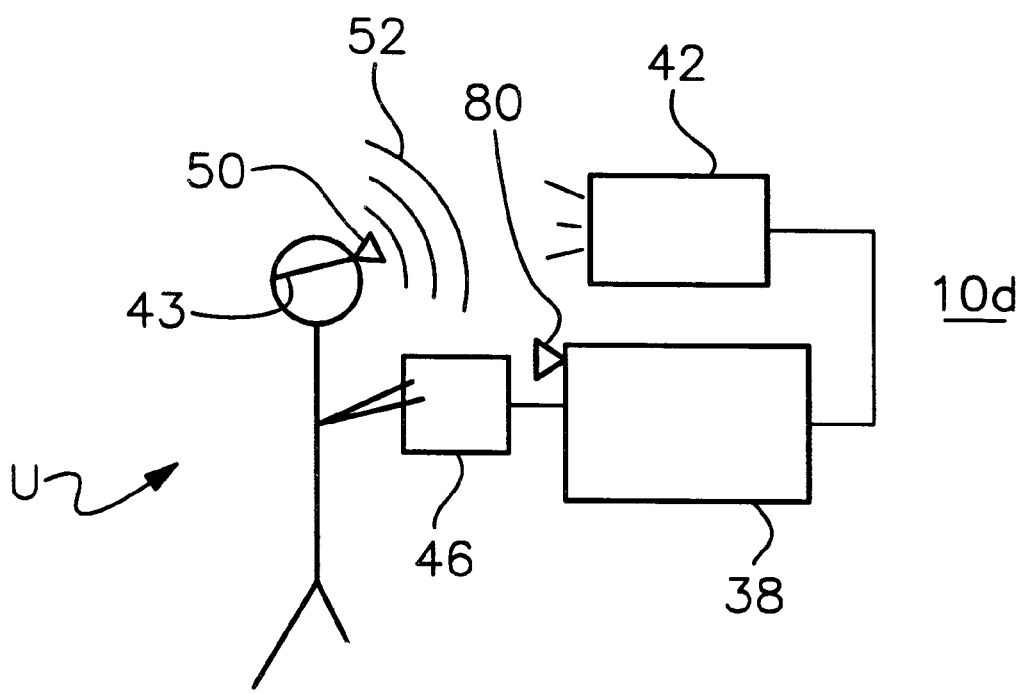
FIG. 6 schematically illustrates yet another embodiment of the present invention, similar to that of FIG. 5, further comprising other modes of input of physical control means.

FIG. 6 schematically illustrates an embodiment 10d similar to that represented in FIG. 5, and further including other active user inputs 46, such as a keyboard, joystick, or pedal.

Figure 7:
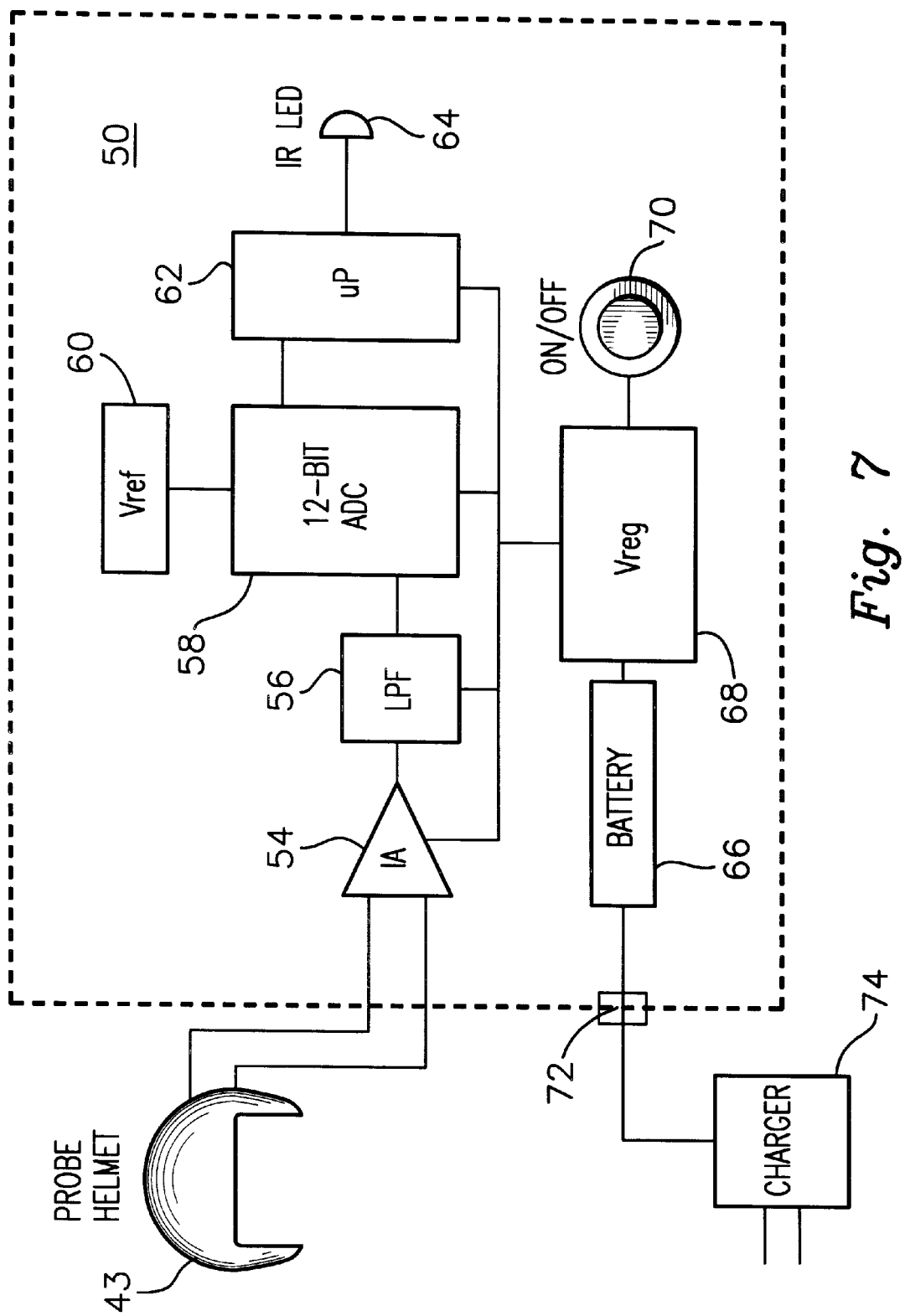
FIG. 7 illustrates an infrared transmitter unit according to the present invention.

FIG. 7 illustrates an embodiment of an infrared transmitter unit 50 according to the present invention. The probe head piece 43 is preferably provided with at least three electrodes. At least one of the electrodes is connected to an inverting amplifier 54 which boosts the normally weak EEG signals to improve detection and/or readability.

The output of the inverting amplifier 54 passes through a low pass filter 56 and is connected to a 12-bit A/D converter 58. At least one of the other electrodes supplies a reference voltage, Vref 60, which is input into the A/D converter 58. At least one other electrode serves as a ground, which is not shown in FIG. 7. Output of the A/D converter 58 is directed to a microprocessor 62 which drives an infrared LED 64 which transmits infrared signals. The unit 50 is further provided with a battery 66 whose output is passed through a voltage regulator 68 which supplies power to the inverting amplifier 54, the low pass filter 56, the A/D converter 58 and the microprocessor 62. An on/off switch 70 is provided to control the flow of electrical power from the battery 66 to the various components of the unit 50. Preferably, the battery 66 is provided with a recharging connection 72, and a battery charger 74 may be connected thereto in order to replenish the battery 66. For example, the charger 74 may convert utility line AC current to a suitable DC recharge supply. Preferably, the battery charger 74 may be disconnected from the remaining circuitry. The low pass filter 56 may be a switched capacitor. The A/D converter 58 may be a 12-bit serial multichannel converter. The microprocessor 62 may be a PIC 12C508 micro controller, which may be used to hold the parts count of the unit to a minimum. The unit 50 may operate at approximately 5 volts with a single supply, Vreg 68. The microprocessor 62 may also include control logic or control circuitry to automatically shut off power from the battery 66, for example after a certain time period has elapsed. The microprocessor 62 is preferably adapted to perform the function of separating the various bands of brain wave activity by a digital technique such as Fast Fourier Transforms (FFT). The filtering must be precise and selective. All of the components of FIG. 7, including the microprocessor 62, are mounted in or on the headpiece 43.

By way of a particular example, one primary electrode which is disposed at either the FP1 (right side) or Sensory Motor Rhythm EEG locations is connected to the inverting amplifier 54, a reference voltage electrode is disposed at the right mastoid area, and a ground electrode is disposed at the left mastoid area.

Conversely, in another particular example, one primary electrode is disposed at FP2 (left side) or Sensory Motor Rhythm locations and is connected to the inverting amplifier 54, while the reference electrode is disposed at the left mastoid area, and the ground electrode is dipsoed at the right mastoid area.

The headpiece 43 may further include a switch which enables the user or the tester to select which electrodes will serve as primary, reference or ground. That is, the headpiece 43 may be provided with a plurality of electrodes connected to a switching means which allow selection of one or more of the electrodes to be electrically connected to a desired component in the headpiece.

Furthermore, the headpiece 43 may comprise a plurality of inverting amplifier 5 and low pass filter circuits (54, 56) to the A/D converter 58 to accommodate more than one primary signal from the electrodes.

Figure 8:
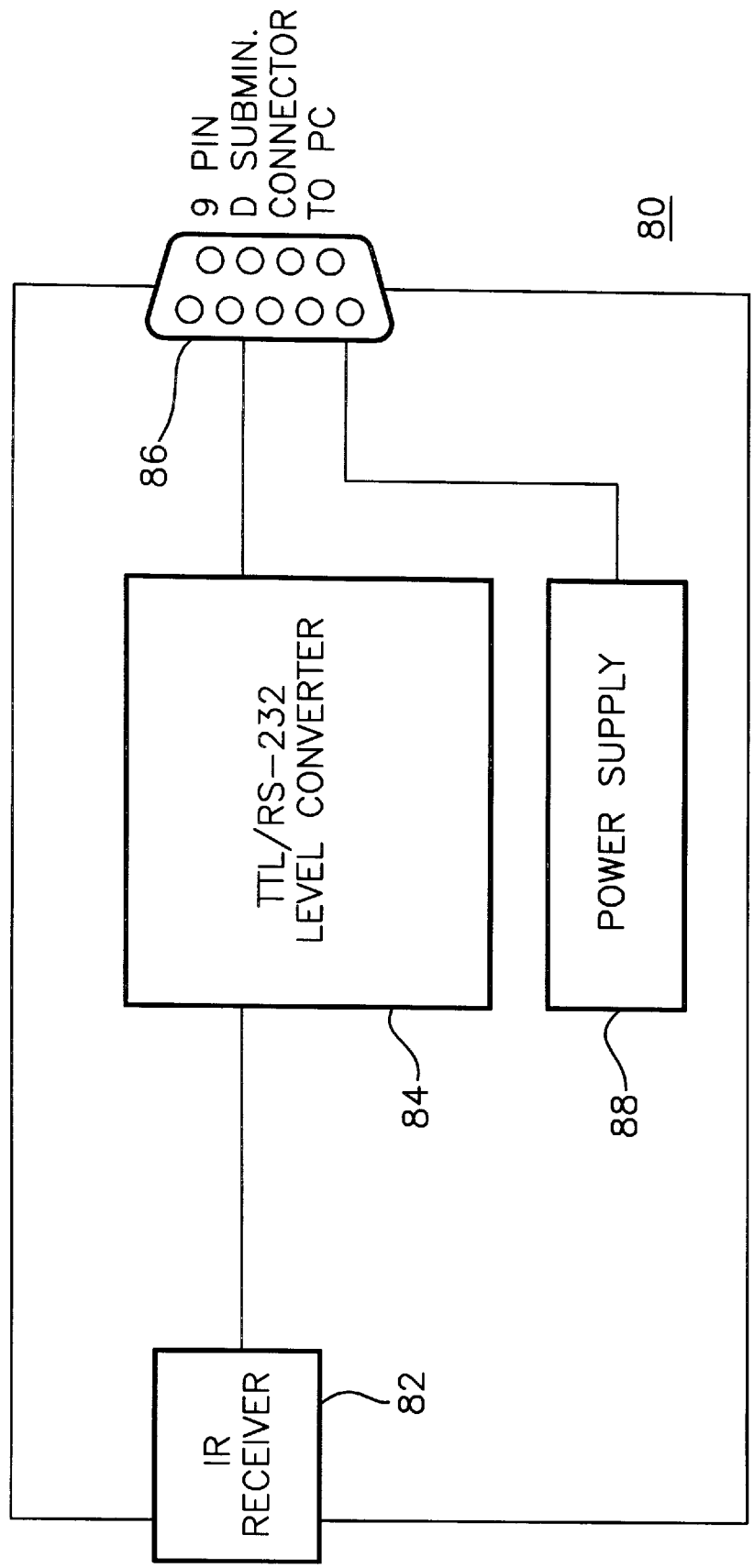
FIG. 8 illustrates an infrared receiving unit according to the present invention.

FIG. 8 schematically illustrates an infrared receiver unit 80 which may be used in conjunction with the above-described infrared transmission unit 50. The infrared receiver module 80 comprises an infrared receiver transducer 82 connected to a TDL/RS232 level converter 84. The converter 84 is connected to a 9-pin D-submin. connector 86 which is adapted for connection with a computer means such as a PC or a video game system. It should be understood that a PC 38 may contain a video game. The infrared receiver unit 80 also comprises a power supply 88 which delivers power to the IR receiver 82 through the 9-pin connector 86 and the RS232 converter 84. The IR receiver transducer 82 is capable of handling at least one input signal which corresponds to a respective EEG electrode signal that emanates from the infrared transmission unit 50. Outputs from the IR receiver transducer 80 are directed into the nine-pin connector 86 for further transmission to a PC 38 or video game system. The nine-pin connector 86 provides a standard serial output to the PC 38 or game module. Preferably, the parts count may thus be kept to a minimum.

The microprocessor 62 of the infrared transmission unit 50 is preferably set at a constant data rate transmission, e.g. at 9600 baud. The receiver 80 parses the constant data flow rate for lower FFT sampling frequencies.

Thus, as represented by FIGS. 5, 7 and 8, the present invention is particularly well suited to allow the user to assume any desired posture or position or to engage in any desired movement while engaging in a biofeedback session without being tethered by any connection lines which might hamper the comfort, freedom of movement, relaxation, attentiveness or concentration of the user. For example, the user may recline, stretch, or adjust before, during, or after sessions or phases of sessions of training or playing.

Referring again to the illustration of FIG. 6, the present invention may further utilize other modes of input or physical control means 46, such as a computer keyboard or joystick, in conjunction with the transmission of EEG signals by infrared carrier, in providing the user U with feedback.

Figure 9:
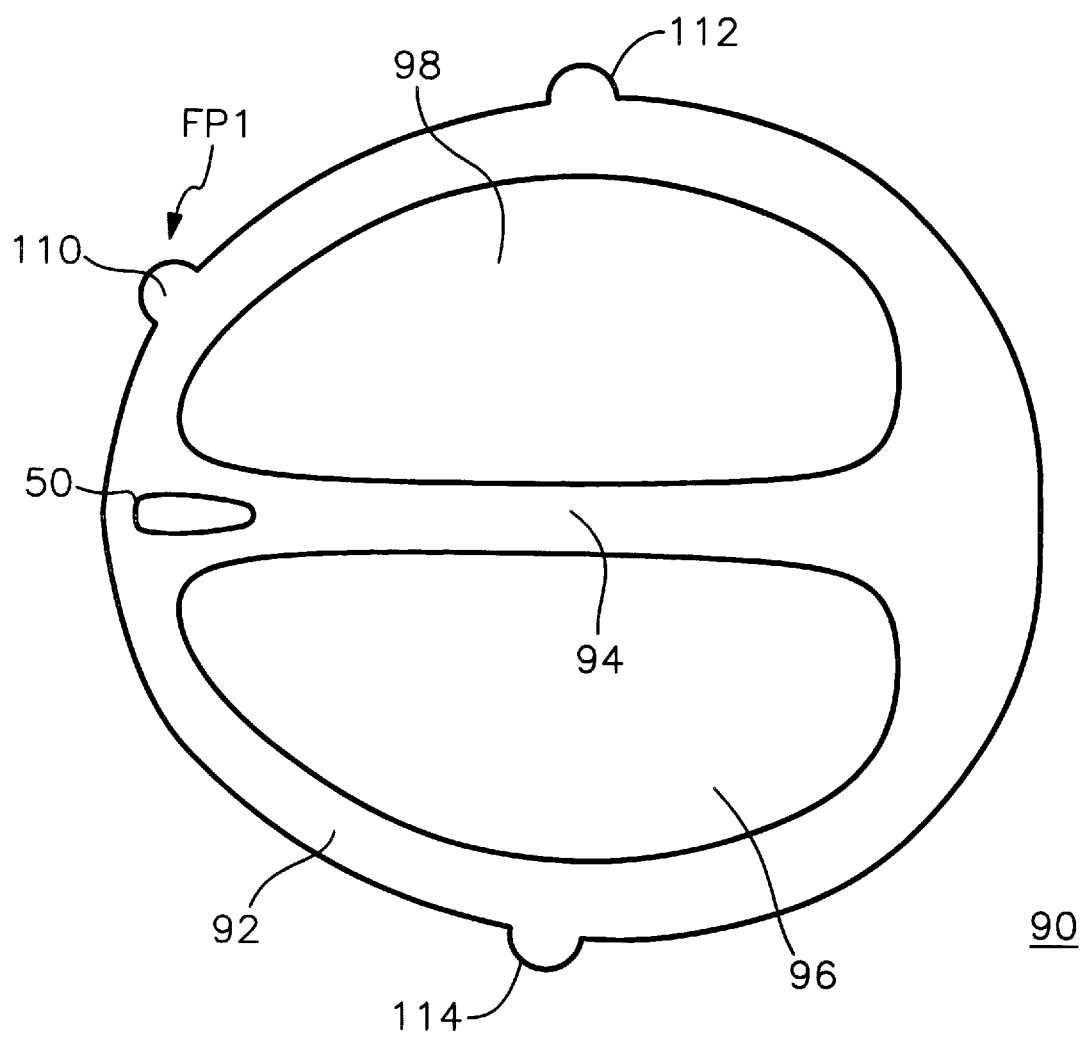
FIGS. 9–11 illustrate a preferred headpiece according to the present invention.
Figure 10:
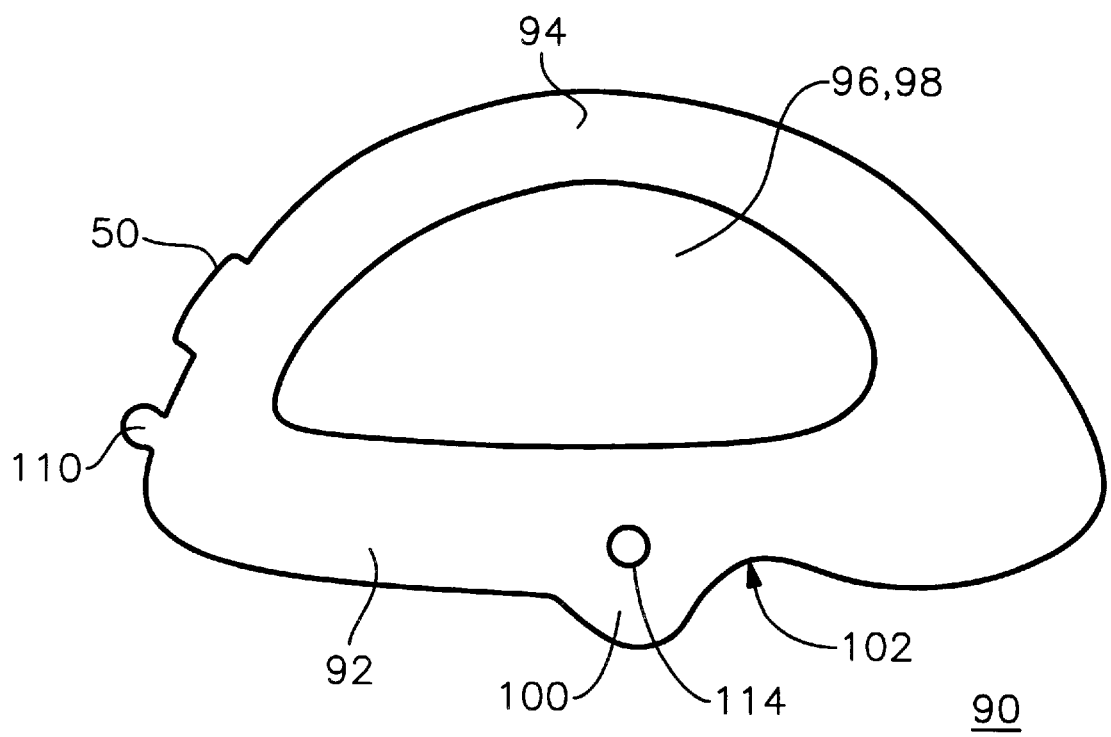
Figure 11:
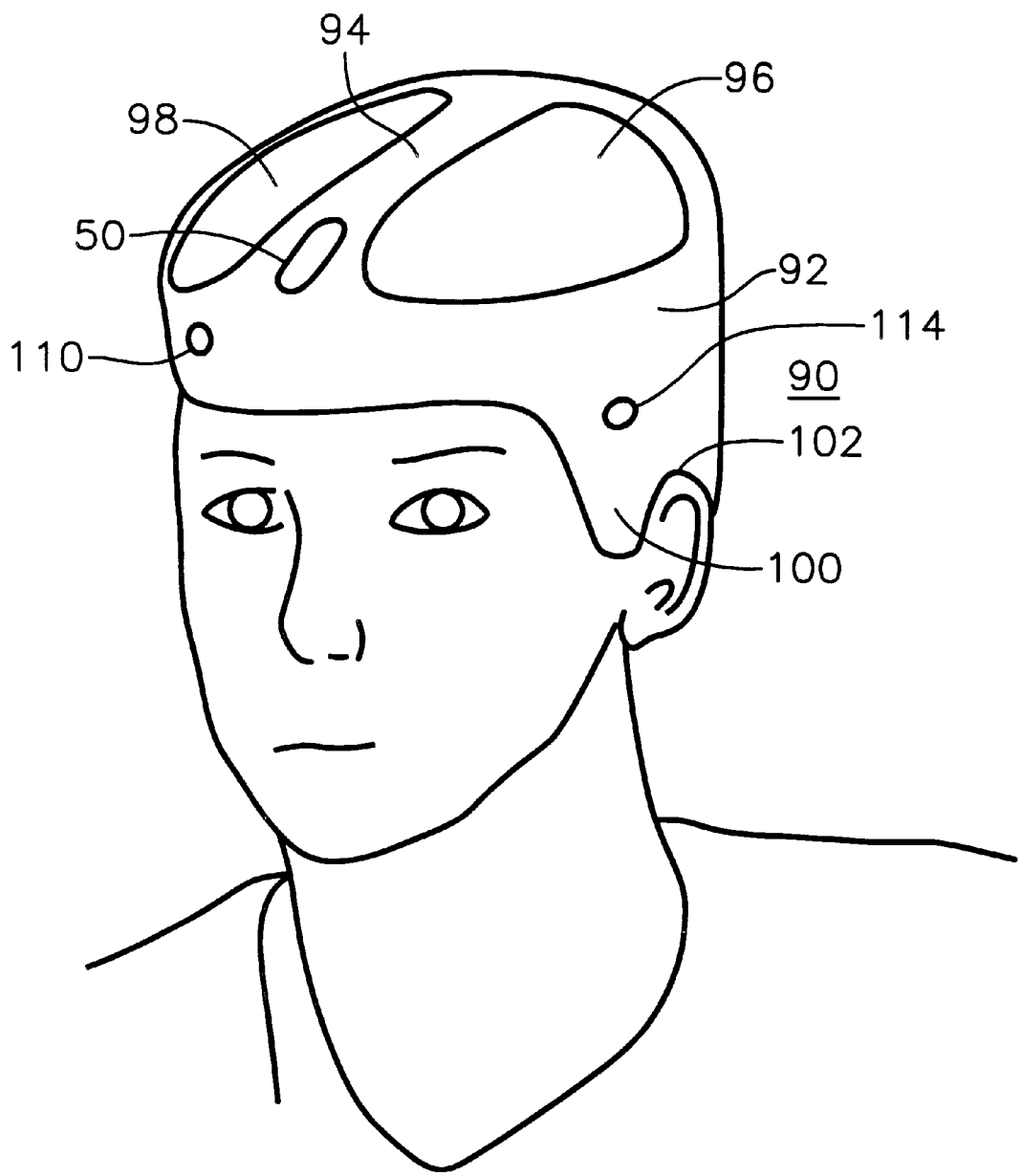

FIGS. 9–11 show a preferred embodiment of a headpiece unit 90 according to the present invention.

As best seen in FIG. 9, the headpiece unit 90 comprises a circumferential portion 92 and a medial portion 94. The headpiece 90 is provided with a pair of generally hemispherically-shaped or lobe-shaped openings 96, 98 defined by the circumferential and medial portions 92, 94. As seen in FIGS. 10–11 the circumferential portion 92 further comprises a pair of downwardly extending portions 100 and a pair of opposed upwardly extending indentations 102. The combination of the downwardly extending portion 100 and the upwardly extending indentation 102 are adapted to fit around the ear of a user, thereby at least partially preventing forward or backward movement or rotation with respect to the head of the user. An infrared transmission unit 50 is disposed on the headpiece, preferably on a forward position on the circumferential portion, although the infrared transmission unit may be disposed in another location on the headpiece 90.

In one embodiment, the headpiece unit 90 further comprises three electrodes or sensors for detecting EEG signals from the head of the user. When used in a biofeedback system according to the present invention, at least one electrode a primary electrode 110 is preferably located on the headpiece 90 corresponding at least generally to at least one of the positions on the head of the user which correspond to the FP1 (above the right eye), FP2 (above the left eye), and/or Sensory Motor Rhythm (forward center of head) EEG locations. The headpiece 90 further preferably comprises at least two additional electrodes: a reference electrode 112 and a ground electrode 114, which are disposed in opposite mastoid areas. For example, if FPI is chosen as a primary electrode 110 site, as shown in FIGS. 9–11 the reference electrode 112 would be disposed at the right mastoid area while the ground electrode 114 is disposed at the left mastoid. Thus, the reference and ground electrodes 112, 114 are positioned on opposite sides of the circumferential portion 92 approximately above the downwardly extending projection. The sensory motor rhythm area is located at the front of the medial portion. If the sensory motor rhythm area is chosen as primary electrode, the reference electrode may be chosen from either mastoid area with the ground electrode disposed opposite the reference.

FIG. 11 illustrates the headpiece unit disposed on the head of a user.

It should be noted that the headpiece 90 may be adapted to receive a plurality of electrodes, even if less than all of the electrodes are electrically connected to the IR transmission unit 50. Thus, the headpiece 90 may be provided with a plurality of holes which accommodate an electrode or electrode tip, and the headpiece 90 may be used even if not all the holes have electrodes disposed therein. It should further be understood that the headpiece 90 further comprises an electrical connection network which is capable of connecting desired electrodes to the IR transmission unit 50.

Furthermore, the headpiece may comprise a means for selectively electrically connecting each electrode to the unit 50.

Thus, the headpiece unit or headset unit 90 may be made according to an ergonomic design which is compatible with the head of the user. The headpiece may be made from lightweight material, such as plastic and/or styrofoam. The symmetric openings 96, 98 in the top of the headpiece 90 contribute to a lightweight design, and further provide ventilation and/or heat transfer to the head of the user, thereby providing comfort and promoting relaxation to the user which is especially helpful during attempts to increase concentration or attention. The circumferential and medial portions, including the downwardly extending projections and the upwardly extending indentations in the circumferential portion, provide the user with a snug but comfortable fit which maintains contact between the electrodes and the head of the user without undue weight, pressure, or discomfort to the user.

The electrodes 110, 112, 114 extend inwardly from the inside surface of the headpiece 90. The electrode tips may be fixedly attached thereto. More preferably, the electrodes are releasably attached to the headpiece 90.

Figure 12:
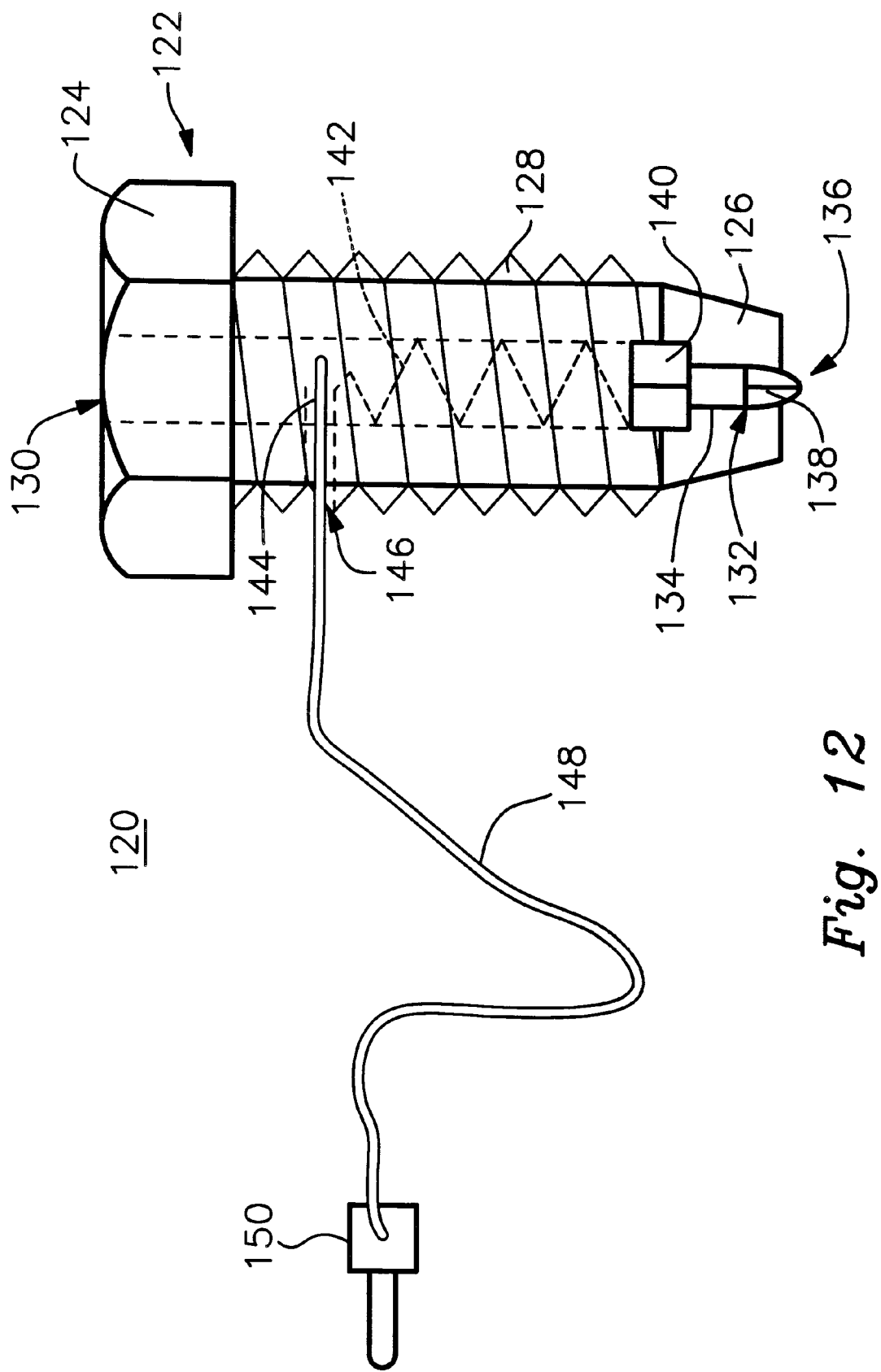
FIG. 12 illustrates a means for releasably mounting an EEG electrode to a headpiece according to the present invention.

FIG. 12 illustrates a preferred embodiment of a means 120 for releasably mounting an EEG electrode on the headpiece 90. A screw 122 having a head 124, a tip 126, and a plurality of threads 128 disposed on the outer surface therebetween, is provided with a bore hole 130 which starts at the top end and extends into the interior of the screw 122 and terminates before reaching the tip 126. A smaller diameter through hole 132, concentric with the bore hole 132, is provided through the tip 126 of the screw 122, wherein an inner shoulder 134 is formed in the interior cavity comprising the bore hole 130 and through hole 132. A probe tip 136 having a narrow diameter portion 138 and a wide diameter portion 140 is inserted into the bore hole 130 at the top of the screw 122, wherein its narrow portion 138 is inserted first. The screw 122 and the probe tip 136 are adapted such that the wide portion 140 of the probe tip 136 rests upon the inner shoulder 134 of the screw 122, and the narrow portion 138 of the probe tip 136 extends through the through hole 132 and projects outwardly from the bottom surface of the screw 122. An electrically conductive, preferably lightweight, compression spring 142 is inserted into the bore hole 130 on top of the probe tip 136, wherein the bottom end of the spring 142 contacts the top of the probe tip 136. An electrically conductive pin 144 is inserted into an opening 146 in the side of the screw 122 for contact with the top end of the conductive spring 142. The pin 144 may extend partially across the bore hole 130 in a cantilever arrangement and have adequate strength to retain the compressive loads imparted by the compression spring 142 and probe tip 136 within the screw 122, e.g. the probe tip 136 may be adapted to withstand cantilever bending moments delivered by the spring 142 and probe tip 136 when the probe tip 136 is pushed back into the screw 122, such as when the bottom of the probe tip 136 is flush with the bottom surface of the screw 122. In another embodiment, the pin 144 may extend fully across the bore hole 130 and be inserted into opposing inner walls of the screw 122. The pin 144 may be substantially round, substantially flat, or some other shape. The pin 144 may be fixedly attached to the screw 122 by adhesive means applied between the pin 144 and the screw 122. The pin 144 may instead be removably attached therefrom, e.g. by providing the pin 144 and screw 122 with mating threads. Alternatively, or in addition, the screw 122 may be provided with a cap which is adapted to fit into the top end of the bore hole 130 and is attached to the remainder of the screw 122 so as to provide a stop means for the compression spring 142 and pin 144. The cap may be fixedly attached to the remainder of the screw 122, for example by an adhesive means applied therebetween, or the cap may be releasably attached to the remainder of the screw 122, for example by providing matching threads on mating surfaces of the cap and the inner wall of the screw 122 which defines the bore hole 130. The pin 144 is then connected to the infrared transmission unit 50, which may be adapted to receive the pin 144 directly, or an additional wire 148, and/or a connecting jack 150 may be provided for connection with the infrared transmission unit 50.

In a particular embodiment, a nylon screw 122 having a coarse thread 128 and a diameter of one half to five eighths inch, is provided with concentric holes 130, 132 drilled out of the center. A stainless steel probe tip 136 with a rounded end is inserted into the cavity. A conductive, lightweight compression spring 142 is inserted behind the probe tip 136. A conductive pin 144 is inserted into a hole 146 drilled into the side of the screw 122. A probe wire 148 is attached to the conductive pin 146. The entire assembly 120 is mounted into a headpiece 90 or helmet made of suitable material, for example plastic and/or styrofoam, which contains holes drilled therethrough for accepting the assembly 120. Optionally, a nylon nut may hold the screw 122 in place.

Figure 13:
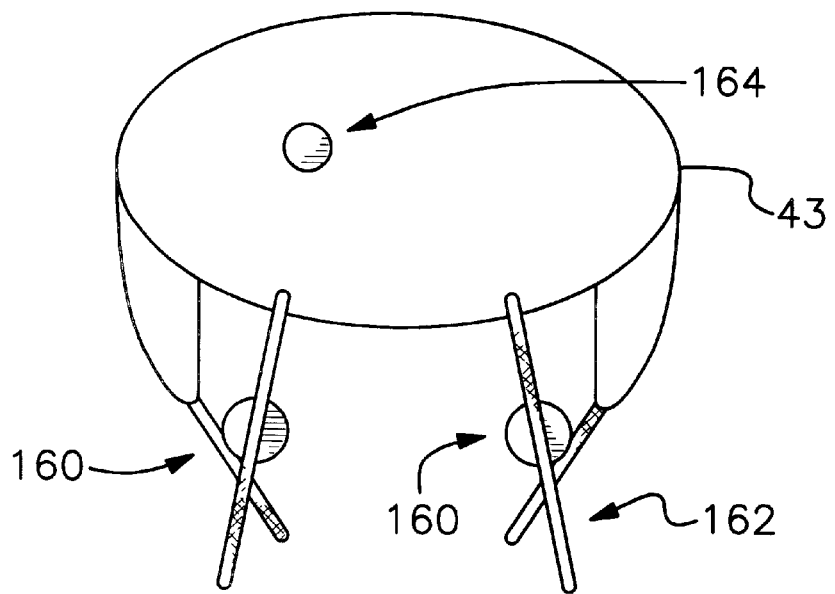
FIG. 13 illustrates an electrode arrangement according to another preferred embodiment of the present invention wherein two electrodes are positioned on the chin straps of a headpiece.

FIG. 13 shows an electrode or sensor arrangement according to another preferred embodiment of the present invention wherein two sensors or electrodes 160 are positioned on the chin straps 162 of a headpiece 43. A top sensor or electrode 164 is preferably internally mounted on the headpiece 43. The headpiece 43 may be, for example, the helmet or headpiece as depicted in FIGS. 7, 9, 10, or 11, as well as other headpieces or the like known to those skilled in the art. Thus, the top electrode or sensor 164 may be held in a desired position in relation to the head of a user by an appropriate headpiece. In this embodiment, two other electrodes or sensors 160 are provided on the respective chin straps 162 of the headpiece 43. In another particular embodiment, the headpiece 43 may have a single chin strap which spans the lower portion of the head of the user, e.g. around or under the chin, so that the two other electrodes 160 may be disposed on the single chin strap at different locations. The chin strap thus preferably promotes contact between the head of the user and the two other electrodes 160, as well as with the top electrode 164 by virtue of the securement of the headpiece to the user by means of the chin strap or straps.

Figure 14:
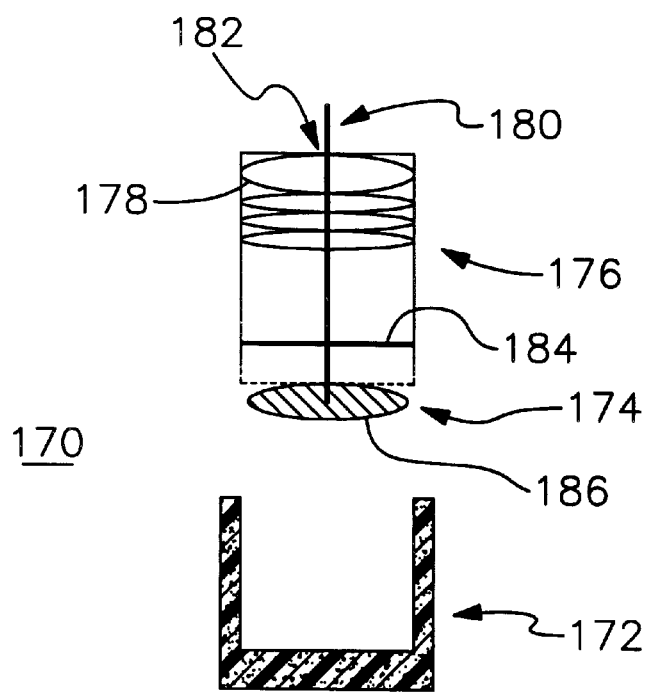
FIG. 14 illustrates an elevational cutaway view of another preferred embodiment of an electrode sensor of the present invention, wherein the sponge cover is shown exploded from the remainder of the electrode.

FIG. 14 illustrates an elevational cutaway view of another preferred embodiment of an electrode sensor 170 according to the present invention. A sponge cover 172 is shown exploded from the remainder of the sensor 170. An electrode 174 is movably disposed within a housing, shown as a cylindrical housing 176. The cylinder 176 may advantageously be made of plastic, for example, for light weight and resistance to moisture. The housing 176 contains a spring 178 for biasing the electrode 174 out of the housing 176. The spring 178 is attached to the stem 180 of the electrode 174. The distal end of the stem 180 of the electrode 174 extends out of an opening 182 provided in the housing 176. An insert 184 attached to the stem 180 contacts part of the housing, or part of the housing 176 contacts the spring 178 and/or the electrode 174, for engagement therewith to contain the spring within the cavity formed in the housing 176 and to limit the travel of the electrode 174. The proximal end of the electrode 174 contacts the user. The proximal end is shown with a contact plate 186 for sensing electrical activity from the user. The contact plate 186 is preferably made from silver/silver chloride or tin, or another suitable conductive material. A sponge cover 172 is provided which fits over the contact plate 186. Gel or a saline solution is preferably contained on or within the sponge cover 172, thereby providing a means for enhancing contact with the user and conducting of electrical activity therethrough, thereby defining an electropatch means. Thus, when the sensor is positioned in proximity to the user, the spring loaded electrode 174 helps to maintain contact with the user even in the event of relative movement between the sensor and the user. Furthermore, the sponge cover 172 impregnated or covered with gel or saline solution provides an electropatch or a resilient contact mount between the user and the sensor 170, so that increased contact and conductivity can be achieved by compression of the sponge cover 172 against a part of the user. It should be understood that the sensor 172 of FIG. 14 may be held in place against the body or head of the user by a headpiece, helmet, or other variety of apparatus, clothing, or other means.

Accordingly, the present invention EEG based biofeedback system may be incorporated as an integral component of an overall plan to develop learning skills, attention arousal, and metacognitive skills with children and adults through the use of interactive software. The present invention thus may be used to assist the user in becoming aware of, developing and understanding his or her own capabilities in. controlling attention and behavior. Thus, in addition to an appropriate learning environment, positive reinforcement, study skills training, counseling, the present invention EEG based biofeedback system enables the user to teach himself or herself to perform to his or her highest potential.

The present invention is not to be limited in scope by the specific embodiment described herein. Indeed, various modifications of the present invention, in addition to those described herein, will be apparent to those of skill in the art from the foregoing description and accompanying drawings. Thus, such modifications are intended to fall within the scope of the appended claims. Additionally, various references are cited throughout the specification, the disclosures of which are each incorporated herein by reference in their entirety.

What is claimed is:

1. A system comprising:
    at least one EEG probe for picking up at least one electrical signal associated with the brain activity of the user;
    a transmitter for converting said electrical signal into at least one infrared signal;
    a mounting device for maintaining said probe in contact with the head of the user and for mounting said transmitter on the head of the user;
    an infrared receiver for receiving an infrared signal from said transmitter and generating at least one EEG signal; and
    a computer including a computer memory encoded with executable instructions representing a computer program capable of causing said computer to present a video game.

2. The system according to claim 1, wherein said computer program is capable of processing said EEG signal as an input into said video game.

3. The system according to claim 2, wherein said computer program is capable of storing said EEG signal and comparing said EEG signal with at least one previously stored EEG signal.

4. The system according to claim 3, wherein said computer program is capable of comparing said EEG signal to a threshold value.

5. The system according to claim 4, wherein said threshold value is stored in said computer memory.

6. The system according to claim 4, wherein said computer program is capable of automatically changing said threshold value based upon a comparison between said EEG signal and at least one previous EEG signal.

7. The system according to claim 4, wherein said computer program is capable of establishing a threshold value based upon at least one previous EEG signal.

8. A method for improving the attention of at least one user by biofeedback, said method comprising the steps of:
    measuring electrical activity of the brain of a user;
    analyzing said measured electrical activity;
    presenting a video game having at least one game output to the user;
    inputting said analyzed electrical activity into said video game;
    presenting to the user at least one feedback signal corresponding to said analyzed electrical activity, wherein said feedback signal is manifested by changes in said game output of said video game; and
    rewarding the user for maintaining at least one level of electrical activity for a predetermined period of time;
    whereby the user is rewarded by sensing said changes in said game output of said video game; and
    whereby said game output assists the user in controlling said electrical activity.

9. The method of claim 8, which further comprises transmitting the measured electrical activity to an analyzer via an infrared signal.

10. A method for improving the attention of at least one user by biofeedback, said method comprising the steps of:
    measuring electrical activity of the brain of user;
    analyzing said measured electrical activity;
    presenting a video game having game output in the form of a plurality of visual images presented to the user;
    inputting said analyzed electrical activity into said video game;
    presenting to the user at least one feedback signal corresponding to said analyzed electrical activity, wherein said feedback signal is manifested by chances in said game output of said video game; and
    rewarding the user for identifying at least one association between at least two of said visual images and for inputting a direct user input corresponding to said association;
    whereby the user is rewarded by sensing said changes in said game output of said video game; and
    whereby said game output assists the user in controlling said electrical activity.

11. The method of claim 10, which further comprises transmitting the measured electrical activity to an analyzer via an infrared signal.

12. A method for improving the attention of at least one user by biofeedback, said method comprising the steps of:
    measuring electrical activity of the brain of a user;
    analyzing said measured electrical activity;
    presenting a video game having at least one primary game output and at least one distracting game output to the user;
    inputting said analyzed electrical activity into said video game;
    presenting to the user at least one feedback signal corresponding to said analyzed electrical activity, wherein said feedback signal is manifested by changes in said game output of said video game; and
    rewarding the user for identifying said primary game output and for inputting a direct user input corresponding to said identification;
    whereby the user is rewarded by sensing said changes in said game output of said video game; and
    whereby said game output assists the user in controlling said electrical activity.

13. The method of claim 12, which further comprises transmitting the measured electrical activity to an analyzer via an infrared signal.

14. A system comprising:

at least one EEG probe for picking up at least one electrical signal associated with the brain activity of a user;

an infrared transmitter for converting said electrical signal into at least one infrared signal;

a mount for maintaining said probe in contact with the head of the user and for mounting said transmitter on the head of the user; and an infrared receiver for receiving said infrared signal from said transmitter and generating at least one EEG signal.

15. The system according to claim 14, wherein said system further comprises:

a computer; and a connection for delivering said EEG signal to said computer.

* * * * *